United States Patent
Densham (10) Patent No.: US 7,608,397 B2
(45) Date of Patent: Oct. 27, 2009

(54) METHOD FOR DETERMINING BIOPHYSICAL PROPERTIES

(75) Inventor: Daniel Henry Densham, Devon (GB)

(73) Assignee: Medical Biosystems Ltd, Totnes, Devon (GB)

( * ) Notice: Subject to any disclaimer, the term of this patent is extended or adjusted under 35 U.S.C. 154(b) by 0 days.

(21) Appl. No.: 11/629,245

(22) PCT Filed: Jun. 13, 2005

(86) PCT No.: PCT/GB2005/002331

§ 371 (c)(1),
(2), (4) Date: Jun. 1, 2007

(87) PCT Pub. No.: WO2005/121363

PCT Pub. Date: Dec. 22, 2005

(65) Prior Publication Data

US 2008/0064035 A1     Mar. 13, 2008

(30) Foreign Application Priority Data

Jun. 11, 2004     (GB) .................................. 0413082.9

(51) Int. Cl.
*C12Q 1/68*     (2006.01)
*C07H 21/02*     (2006.01)
*C07H 21/04*     (2006.01)

(52) U.S. Cl. .......................... 435/6; 536/23.1; 536/24.3

(58) Field of Classification Search ............... 435/6; 536/23.1, 24.3
See application file for complete search history.

(56) References Cited

FOREIGN PATENT DOCUMENTS

WO     WO 1999/05315 A     2/1999
WO     WO 2005/007887 A     1/2005

OTHER PUBLICATIONS

Russo et al., Atomic force sensing of light-induced protein dynamics with microsecond time resolution in bacteriorhodpsin and photosynthetic reaction centers. Journal of Structural Biology 119 : 158-164 (1997).*
Di Carlo, Dino et al. "Nanograp—based dielectric immunosensing" Transducers 2003, International Conference on Solid-State Sensors, Actuators and Microsystems, Digest of Technical Papers, 12th, Boston, MA, United States, Jun. 8-12, 2003, vol. 2, 1180-1183 Publisher: Institute of Electrical and Electronics Engine, 2003.
Hansen, Karolyn M. et al. "Cantilever-Based Optical Deflection Assay for Discrimination of DNA Single-Nucleotide Mismatches", Apr. 1, 2001, *Anal. Chem.*, vol. 73, No. 7, pp. 1567-1571.
Lee, Joon Sung et al. "Nanogap Capacitors for Label Free DNA Analysis", 2002, *Mat. Res. Soc. Symp. Proc.* vol. 729, pp. 185-190.
Ros, Robert et al. "Single molecule force spectroscopy on ligand-DNA complexes: from molecular binding mechanisms to biosensor applications", Aug. 26, 2004, *Journal of Biotechnology*, vol. 112, No. 1-2, pp. 5-12.
Yi, Mingqiang et al. "Theoretical and experimental study towards a nanogap dielectric biosensor", Jan. 15, 2006, *Biosensors & Bioelectronics*, Elsevier Science Publishers, Barking, GB, vol. 20, No. 7, pp. 1320-1326.

* cited by examiner

*Primary Examiner*—Ethan Whisenant
(74) *Attorney, Agent, or Firm*—Saliwanchik, Lloyd & Saliwanchik (57) ABSTRACT

The invention is a method for detecting a change in the conformational or energetic state of a molecular species, comprising the steps of: (i) immobilizing the molecular species, under conditions suitable for the reaction to occur; (ii) contacting at least part of the molecular species with a localized electromagnetic field; and (iii) detecting a change in dielectric constant during or after the reaction, to thereby detect a change in the conformational or energetic state of the molecular species.

21 Claims, 4 Drawing Sheets

METHOD FOR DETERMINING BIOPHYSICAL PROPERTIES

This application is a National Stage Application of International Application Number PCT/GB2005/002331, filed Jun. 13, 2005; which claims priority to Great Britain Application No. 0413082.9, filed Jun. 11, 2004.

FIELD OF THE INVENTION

This invention relates to a method for measuring the dynamic conformational or energetic state of a molecular species. This invention is particularly useful in polynucleotide sequencing techniques.

BACKGROUND OF THE INVENTION

The ability to study biological processes at the level of a single molecule is of great scientific importance. One of the primary goals of molecular and cellular biology research is to understand the biophysical properties of biological systems, e.g. nucleic acids and proteins, and their dynamic interactions with their environment. Traditional visualisation of single molecules using techniques such as X-ray crystallography and NMR spectroscopy are limited by their static observations and require ensemble imaging that is not strictly representative of a single molecule. New techniques are therefore required that allow single molecules to be monitored with high sensitivity and resolution.

Recent advances in imaging techniques have made it possible to observe the dynamic behaviour of a single molecule (see, for example, Ha et al., Proc Natl Acad Sci USA. 1999; 96(3):893-8). However, these approaches have generally been based on indirect methods relying on the detection of fluorescent dyes. These dye systems suffer from a number of drawbacks, such as blinking, spiking and photobleaching, which limit the observations which can be made.

Photobleaching is a well documented phenomenon in fluorescent dye systems. All dye systems have the ability to absorb a limited number of photons before the fluorescent dye is no longer visible to the observer, i.e. it has been photobleached. If the dye is conjugated to a molecule under study, the molecular kinetics, dynamics and reaction pathway under observation will no longer be visible. This is a particular problem in the study of polynucleotide processive enzymes, where conformational changes resulting from the interaction with a polynucleotide can be monitored to allow polynucleotide sequencing, as outlined in WO-A-99/05315.

Photobleaching is a problem in all high-resolution assays involving fluorescent dye molecules (J. Histochem. Cytochem., 1999; 47:1179), especially when such dyes require repeated excitation at high frequency in order to obtain the information about the fluorophore required, for example Fluorescent Lifetime Imaging Spectroscopy (FLIMS) and Flourescent Polarisation Anisotropy measurements.

Blinking is a phenomena that has been observed in conjunction with photobleaching and is a considerable limitation in the context of experiments requiring fluorescent labels. Blinking events, a particular problem in relation to quantum dots or nanocrystal dyes, are unpredictable and can add error to experimental data. Such 'quantum' events are of particular relevance to single molecule measurements.

Furthermore, problems are associated with attaching "large" fluorescent labels to pharmaceutically important molecules. These problems are enhanced in small molecule systems where the labels are larger with respect to the molecule under study.

Non-fluorescence based techniques such as Surface Plasmon Resonance (SPR) and Evanescent Spectroscopy are therefore preferred for detecting single molecules. However, these techniques have, to date, typically operated on a multi-molecule scale due to a lack of sensitivity. Attempts to improve sensitivity have been made by monitoring changes in molecular dielectric information directly, to produce dynamic conformational information. One such approach is detailed in WO-A-01/18246, wherein a device is used to measure changes in the capacitance of the fluid, gas, molecule, particle or cell under study as it passes through the device. However, the transient nature of this system allows only relative flow-through data to be obtained, and not conformational data.

The ability to monitor real-time conformational changes of a single molecule is particularly applicable in the field of polynucleotide sequencing, where it is desirable to monitor the polynucleotide processive enzyme to detect the interaction(s) with the target polynucleotide, for example the addition of each successive base. This removes the need for labelled nucleotide substrates (particularly fluorescently-labelled), which can interfere with the catalytic activity of the enzyme, reducing the sequencing rate and increasing the misincorporation rate. A system capable of real-time sequencing without the use of labelled nucleotides or nucleotide analogues would therefore offer the considerable advantages of faster sequencing, longer read length and lower error rates.

New techniques are therefore required that are able to monitor and record single molecule dynamic conformational changes with high resolution and sensitivity, and avoid the problems associated with fluorescence. Such a technique could be used for protein characterisation, ultra-sensitive chemical analysis and rapid DNA sequencing.

SUMMARY OF THE INVENTION

The present invention is based on the realisation that the conformational or energetic state of a molecular species can be obtained by immobilising the molecular species within a spatially localised and/or enhanced electromagnetic field and directly monitoring molecular dielectric information. The dielectric constant of the molecular species will be altered as the molecular species participates in a reaction.

According to a first aspect of the present invention, a method for detecting a change in the conformational or energetic state of a molecular species comprises the steps of:

(i) immobilising the molecular species, under conditions suitable for the reaction to occur;

(ii) contacting at least part of the molecular species with a localised electromagnetic field; and (iii) detecting a change in dielectric constant during or after the reaction, to thereby detect a change in the conformational or energetic state of the molecular species.

In particular, the method can be used to monitor a polynucleotide processive enzyme, allowing polynucleotide sequencing to be carried out with small amounts of nucleic acid, even single nucleic acid template molecules, which eliminates the need for amplification prior to sequencing. By avoiding the labelling of the native nucleotide substrate, the present invention can be used to monitor with high accuracy a native polynucleotide processive enzyme system. Long sequence read lengths can be obtained and secondary structure considerations minimised. These long read lengths eliminate the need for extensive fragment reassembly. Further, the limitation of read length at the single molecule level as a function of photobleaching or other unpredictable fluorescence effects is circumvented, giving a regenerative system.

DESCRIPTION OF THE DRAWINGS

The present invention is described with reference to the accompanying drawings, wherein.

DETAILED DESCRIPTION OF THE INVENTION

The present invention relates to the measurement of the dynamic conformational and/or energetic state of a molecular species, through the detection of changes in the dielectric constant of the molecular species within a spatially localised electromagnetic field.

The dielectric constant is a number relating to the ability of a material to carry alternating current to the ability of vacuum to carry alternating current. The capacitance created by the presence of a material is directly related to the dielectric constant of the material. When an electromagnetic wave travels through a dielectric, the velocity of the wave will be slowed down. The wave will behave as if it had a shorter wavelength. The measurement of these effects is known as the dielectric constant.

As used herein the term "conformational state" refers to the change/alteration of a biological species structural conformation. For example, if the biological species is an enzyme, the structural conformation of the enzyme changes depending on whether or not it interacts with its substrate.

The term "energetic state" is intended to refer to the charge distribution of a molecule (electromagnetic permettivity).

As used herein, the term "molecular species" refers to any molecule, molecular complex or particle that has the capacity for dynamic conformational and/or energetic change. Preferably, the molecular species is a biological molecule, preferably a protein (including peptides and polypeptides), nucleic acid (including oligonucleotides and polynucleotides), carbohydrate or lipid, or any combination thereof. More preferably, the biological molecule is a protein, such as an enzyme. Most preferably the enzyme is a polynucleotide processive enzyme.

The term "polynucleotide processive enzyme" as used herein is to be interpreted broadly, referring to any enzyme that interacts with and processes along a polynucleotide. In a preferred embodiment, the enzyme is a polymerase enzyme of any known type. For example, the polymerase may be any DNA-dependent DNA polymerase. If the target polynucleotide is a RNA molecule, then the polymerase may be a RNA-dependent DNA polymerase, i.e. reverse transcriptase, or a RNA-dependent RNA polymerase, i.e. RNA replicase. In a preferred embodiment of the invention, the polymerase is T4 polymerase. In a further preferred embodiment of the invention, the polymerase is either E. coli polymerase III holoenzyme (McHenry, Ann. Rev. Biochem. 1988; 57:519), T7 polymerase (Schwager et al., Methods in Molecular and Cellular Biology, 1989/90; vol. 1(4): 155-159), or bacteriophage T7 gene 5 polymerase complexed with E. coli Thioredoxin (Taboretal., J. Biol. Chem., 1987; 262:1612-1623). Each of these polymerase enzymes allows binding with the target polynucleotide to occur with high processivity and fidelity, and therefore maintains a polymerase-polynucleotide complex even when polymerisation is not actively taking place.

Alternatively, the polynucleotide processive enzyme may be a helicase enzyme, primase, holoenzyme, topoisomerase, gyrase enzyme or combinations thereof. Using a helicase reduces the problem of secondary structures that exist within polynucleotide molecules, and helicases also offer the ability to directly sequence double-stranded DNA at room temperature, as disclosed in WO-A-00/60114.

The term "polynucleotide" as used herein is to be interpreted broadly, and includes DNA and RNA, including modified DNA and RNA, as well as other hybridising nucleic acid-like molecules including synthetic analogues such as peptide nucleic acid (PNA) and locked nucleic acid (LNA).

As the polynucleotide processive enzyme processes along the target polynucleotide, its conformation will change depending on the nucleotide on the target with which it is brought into contact. The enzyme interacts with a single target polynucleotide molecule; the activity of the enzyme on the target polynucleotide to be sequenced can therefore be followed in real-time, thereby identifying the order of bases on the target polynucleotide. When the enzyme is a polymerase, a conformational change is brought about when the polymerase incorporates a nucleotide into a nascent strand complementary to the target polynucleotide. The conformational change for each of the different nucleotides, A, T, G or C will be different and therefore measuring the conformational change will identify which nucleotide is incorporated, this process is described in WO-A-99/05315.

The molecular species is localised in a fixed position. Preferably, this localisation occurs by immobilisation of the molecular species onto a solid support. Immobilisation may be via covalent or non-covalent bonding. Preferably, the immobilised molecular species retains its function, for example an enzyme retains its enzymatic activity. Immobilisation of biological molecules on solid supports is well known in the art. Suitable solid support materials include silicon, glass, ceramics and metals, amongst others. The choice of support will depend on the molecule to be immobilised and the detection method employed. For example, Surface Plasmon Resonance (SPR) detection requires a metal surface. The support is preferably a planar surface.

In a preferred embodiment, the surface is a metal capable of sustaining a propagating plasmon wave, and immobilisation is carried out using selective modification of self-assembled mono-layers (SAMs) by an AFM or NSOM probe. Such modifications can be used with either non-specific absorption of the molecule to the gold surface in which the SAM has been selectively removed, or by the attachment of the molecule to a specifically modified SAM using a functional group. Alternatively, immobilisation using standard amine coupling procedures may be used, with attachment of ligand-associated amines to, for example, a dextran or N-hydroxysuccinimide ester-activated surface. Examples of procedures used to immobilise biomolecules to optical sensors are disclosed in EP-A-0589867 and Löfas et al.; Biosens. Bioelectron. (1995) 10:813-822.

The invention requires that at least part of the molecular species is immobilised within a localised electromagnetic field. Preferably, the localised electromagnetic field is enhanced. The molecular species can be covalently attached to a solid support at areas of localised field enhancement, for example between two electrodes or near areas of plasmon wave enhancement. It will be appreciated by one skilled in the art that due to the dimensions involved, the electrodes can be position on a micro- or nano-scale structure.

Any known method of localising an electromagneticwave to a molecular species and monitoring the dielectric constant can be used in the present method.

A first method of applying localised radiation to the immobilised molecular species of interest is by applying an electrical signal between two electrodes, between which at least part of the molecular species under study is immobilised. It is preferred that the applied electrical signal is alternating (A/C) in nature. Any frequency may be applied, although it is preferred that the frequency applied between the electrodes is in the range of 1 Hz to 100 GHz. The change in the dielectric constant associated with the conformational change in the molecular species can be detected by measuring a change in the impedance of the electrodes as will be appreciated by those skilled in the art. An alternative method for detection of change in dielectric constant consists of measuring the change in total capacitance between the electrodes. An A/C bridge may be employed in order to determine the change in total capacitance. Preferably, a nanostructure consisting of two electrodes separated by a space in which the molecule of interest is immobilised is used. Typically, the space between the electrodes is between 1 nm and 1 micrometer but can range between 1 nm and 1 mm. The spacing of the electrodes is preferably approximate to the range of the molecular species under study (1-500 nm), such that the molecular species substantially fills the space between the electrodes. The electrical current is applied to one of the electrodes.

Figure 1:
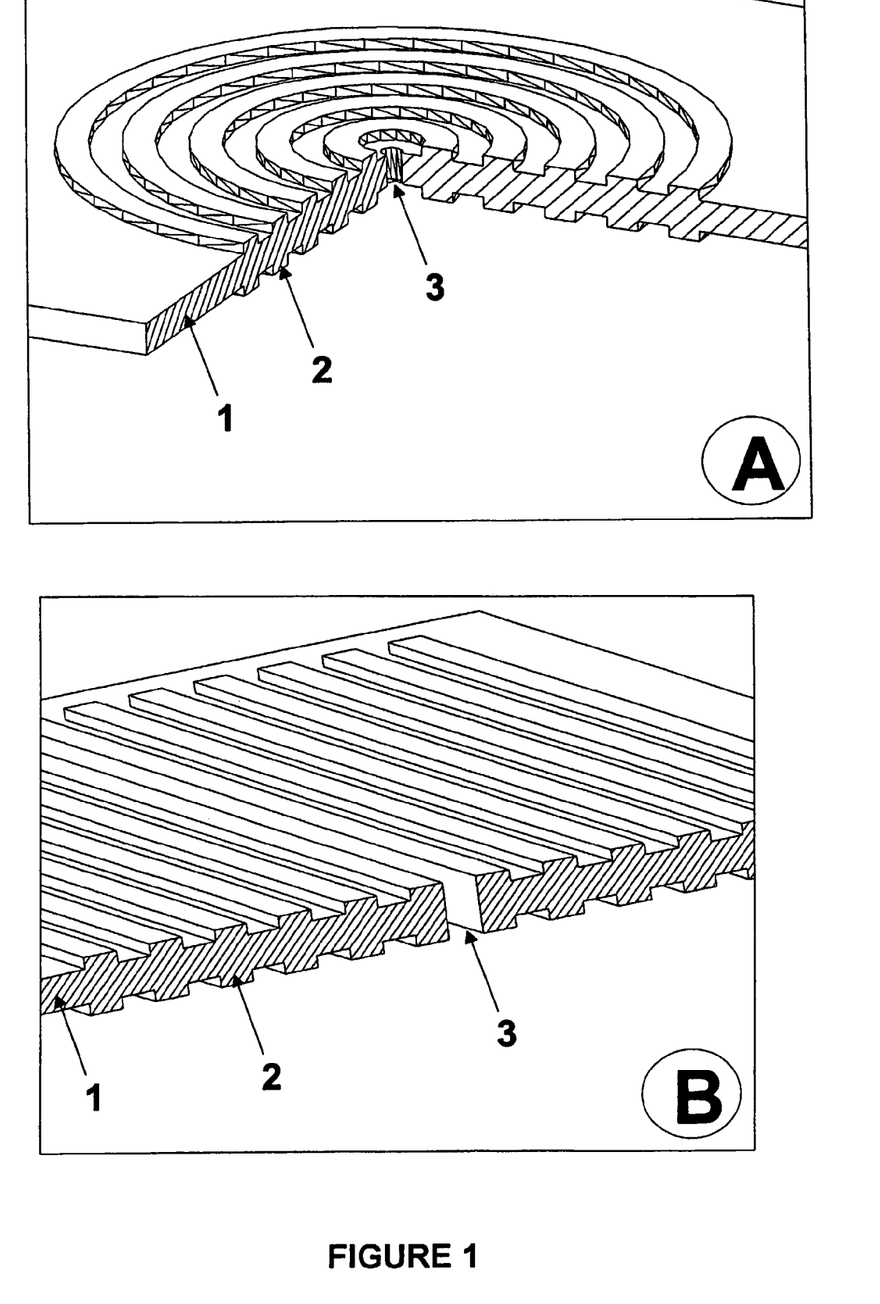
FIG. 1 shows possible plasmon concentrator geometries (A—concentric, B—rectangular)

A second method of applying localised radiation to the immobilised molecular species is by the use of Surface Plasmons. Surface Plasmons (or Surface Plasmon Polaritons) are well understood in the art to be electromagnetic modes constituted by a light field coupled to a collective electron oscillation propagating along an interface between a metal and a dielectric. In this embodiment, a Surface Electromagnetic Wave (SEW) concentrator structure can be used to enhance the SEW. The molecular species is immobilised within, or in close proximity to, the SEW concentrator structure, so that at least part of it is within the region of localised field enhancement. Any structure suitable for concentrating SEW waves may be used. Preferably, the SEW concentrator is an integrated plasmon wave concentrator, microfabricated in a metal layer capable of supporting Surface Plasmon Resonance. Most preferably, the SEW concentrator is microfabricated in a gold layer (FIGS. 1A &B). The radiation applied in this embodiment is preferred to be in the visible or infrared range in order to excite plasmons on thin gold layers. The gold nanostructure is designed so that the surface plasmon wave travelling across it is concentrated locally in a defined submicron region or regions. A suitable surface plasmon concentrator takes the form of a subwavelength hole surrounded by a set of circular grooves, with dielectric layers above and below (see FIG. 1A). Alternatively, the concentrator structure can take the form of a sub-wavelength slit surrounded by a set of linear grooves (FIG. 1B). This system allows measurements of dielectric constant to be carried out efficiently.

An array of electrodes or concentrator structures on a chip surface may be created, such that a number of conformational monitoring experiments may be carried out in parallel. This array structure may be integrated with a series of microchannel flow channels, arranged so that microfluidics may be employed to deliver different reactants to different concentrators/electrodes on the same chip surface.

The first and second methods of applying localised radiation (electric field and plasmonic enhancement modes respectively) may be combined in a single system. This has the advantage of increasing the signal-to-noise ratio, a critical factor in single molecule detection systems. This signal enhancement occurs because an electrical field within the vicinity of a surface plasmon will cause attenuation of the field and/or the creation of scattering centres at points in space relative to the electrical field intensity. This leads to two useful characteristics. Firstly, the intensity of emitted light (and hence signal intensity) from the plasmon field is largely increased from a point relative to the electrode geometry.

Secondly the emitted light signal from the field of interest (the molecular species) will be modulated with a frequency approximately equal to that of the applied electrical field. The applied A/C frequency may be between 1 Hz and 100 GHz. This frequency modulation allows signal extraction and increases the signal to noise ratio. The application of the electrical field also allows for "tuning" of the applied field in such a way that resonant frequencies at which the molecular species responds can be more easily modulated.

Figure 2:
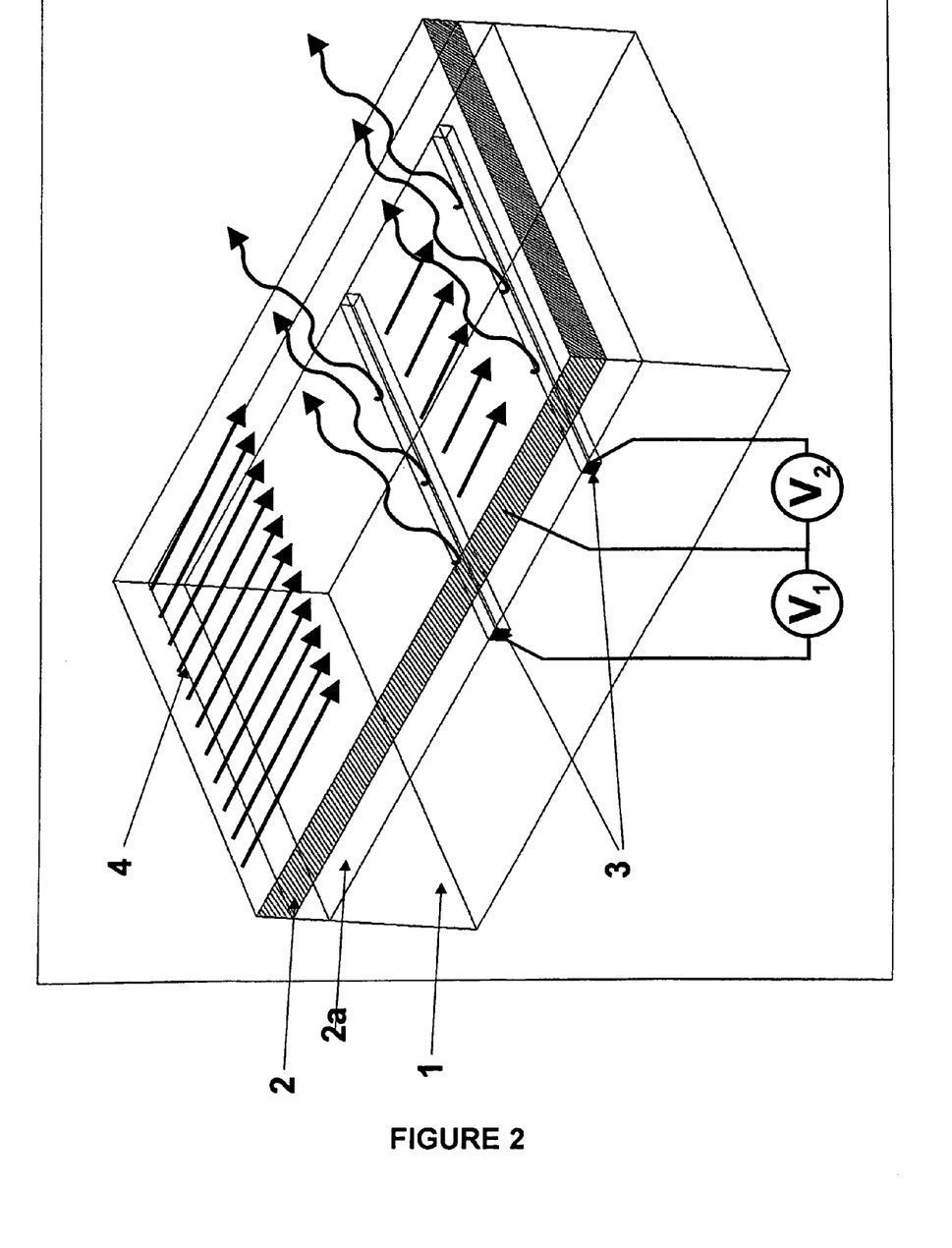
FIG. 2 shows the scattering of plasmons by means of a local change in the dielectric constant induced by an applied electric field using buried electrodes.

In a preferred embodiment (FIG. 2), electrodes are "buried" in the plasmon field conducting layer. The buried electrodes do not interfere with the fluid flow over the surface layer, which is preferably gold, and prevent the presence of the electrodes from preventing or "collapsing" the surface plasmon field travelling along the surface of the gold film. An embedded array of electrodes under a gold plasmon supporting surface layer will allow the addressing or "selection" of specific regions on the chip surface where single molecules are immobilised. This can be ascertained by selectively activating different embedded electrodes such that different scattering centres are illuminated on the chip surface. By then altering the local environment of the molecule on the surface, conformational changes can be induced in the molecule which may then be observed via attenuation of the scattered/plasmon signal, if such signal originates substantially within the region of the molecular species. This can then be used as confirmation of the location of a single molecule at or near the embedded electrode location. The embedded electrode may then be used to further acquire further conformational data about the molecular species via continuous monitoring.

A third method of creating localised electromagnetic field enhancement is achieved on a surface plasmon surface using a metalised Scanning Probe Microscope/Atomic Force Microscopy (SPM/AFM) tip. Dielectric changes are detected by monitoring changes in the scattered light intensity maximum relating to a particular tip-surface (sphere-plane) structure. This embodiment is an adaptation of a scanning plasmon near-field microscope operating in the tapping mode of an atomic force microscope. In this set-up, the electromagnetic resonance is of greater intensity when the tip and surface are noble metals, which are therefore preferred. At the electromagnetic-resonance in such a structure, the dimension of the light field localisation is of the order of $L \approx (2\,dR)^{1/2}$, where d is the tip-surface distance and R is the tip radius. This has advantages due to the fact that at d<<R the resolution of the near-field images is less than tip radius (L<R)(Konopsky, 2000; Opt. Com.; 185: 83-93). This leads to a highly localised/enhanced electromagnetic field.

Figure 3A:
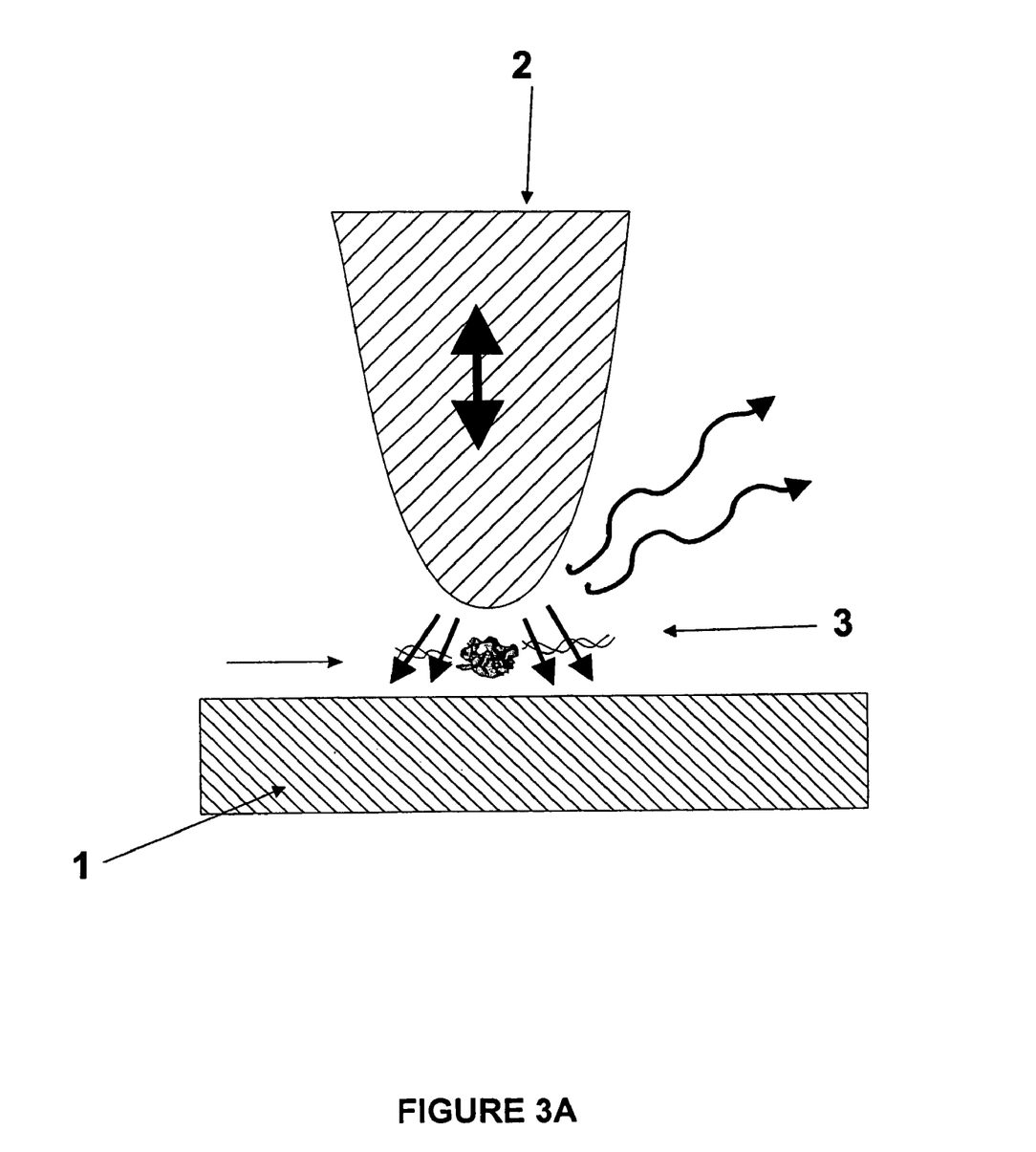
FIG. 3(a) shows single-molecule monitoring based on the concentration of an electric field under a scanning probe microscope (SPM) tip.
Figure 3B:
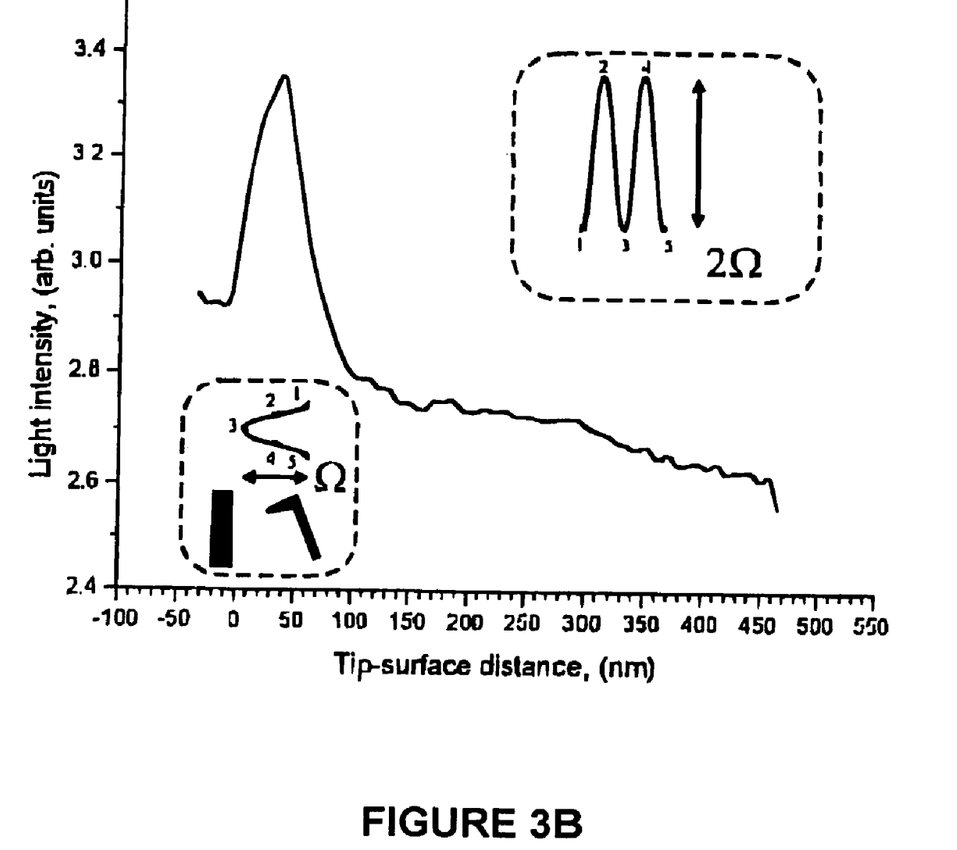
FIG. 3(b) shows the intensity of the scattered light detected at the second harmonic vs. tip height above the surface.

A molecule can be immobilised on a surface, with the tip positioned over it, operating in stationary mode (still tapping) (FIG. 3). Conformational changes of the enzyme will result in localised dielectric changes within at least a part of the localised electromagnetic field (the surface plasmon), resulting in a scattered and/or reflected light signal. Therefore, by monitoring the light emitted at the second harmonic of the tapping frequency, a maximum will be observed. The position of this maximum (tip-surface distance plotted against light intensity) will reflect the dielectric constant between the tip and surface (sphere-plane) and movements of the maximum will reflect conformational changes in the localised molecular species.

For all embodiments utilising surface plasmon resonance, resonant distance information for the molecular species can be used to construct concentrators of the correct dimensions to create concentrator and/or electrode/plasmon structures, at or near the molecular species resonance condition. Several limitations of this configuration, however, are foreseen. The central problem when utilising "conventional" AFM/SPM cantilevers to enhance a surface plasmon is that a large number of molecular species (i.e. biological molecules) require a fluid environment to function correctly. The cantilevers employed must therefore be operated in fluid, limiting the resonant frequency of the cantilever to around 15-30 KHz, due to damping conditions. The second harmonic of such a set-up results in a relatively low sampling frequency with respect to relevant biological events which occur on the milli to microsecond time frame (multiple samples must also be considered in order to increase signal to noise ratio). Other negative effects when employing conventional AFM/SPM set-ups in such a configuration include unwanted force/noise effects on the tip due to the fact that many biological molecules function better when placed in a flow stream. A flow stream creates forces on the cantilever which in turn produces noise in the system. A further problem is that conventional AFM/SPM systems utilise piezo-electric scanners/actuators, which results in a small lateral drift between the tip and sample/molecule surface. For most, even high-end, applications such drift (in the order of a few nanometers) is either insignificant or can be tolerated. However, in the case of the dielectrically driven measurement of conformational change, this drift is a major drawback. A few nanometers on the scale of a single molecule is very large and such noise negatively impacts upon signal-to-noise ratio.

A solution to this problem is based on the realisation that micro/nano-fabricated structures are mechanically more stable at smaller dimensions and therefore less prone to mechanical drift. Further, micro cantilevers with two attachment points can have resonant frequencies in the range of tens of megahertz. A preferred embodiment of the present invention, therefore, is the use of gold (or other plasmon supporting material) coated micro/nano-cantilevers for the achievement of conformational monitoring via the phenomenon of sphere-plane electromagnetic resonance. Preferably, the cantilevers will possess a gold protrusion of less than 30 nm which will act as a sphere from which the electromagnetic field will emanate. The device is driven at its resonant frequency and illuminated from below or the side by a light source capable of producing surface plasmons on the metallic surfaces of the cantilever-plane system.

In all embodiments described herein, it is foreseen that in order to increase modulation of the dielectric properties of the molecular species it is possible to attach a metallic particle at or near the molecular species of interest. Preferably, the particle is a nanoparticle. More preferably, the nanoparticle is attached to the molecular species. The nanoparticle can be attached to the molecular species in a number of ways known in the art. A preferred method of attachment is to cover the surface of the nanoparticle with a Self Assembled Monolayer (SAM), as known in the art, and then to covalently link the particle to the molecular species. A number of techniques are well known in the art in order to provide covalent linkages. For example, the covalent linkage can be formed between the SAM side group and a cysteine residue within the (protein) molecular species of interest.

In a further embodiment within the context of sphere-plane electromagnetic resonance, the tip of the cantilever (sphere) may take the form of an actual sphere. This sphere oscillates above the surface of the plane plasmon-supporting surface with the molecular species immobilised thereon in an analogous fashion to the resonant oscillation of an AFM/SPM cantilever. This oscillation can be created by the application of a "laser trap" as is well known in the art. This trap can be made to move the cantilever up and down above the molecule on the plasmon supporting surface. Alternatively, the cantilever can be made of a magnetic sphere covered with a layer of gold or similar plasmon supporting material. By control of an external magnetic field, the metal nanoparticle can again be made to execute a motion analogous to the movement of a cantilever tip moving into and out of the sphere-plane resonance distance. The position of maximum intensity of the output light can be again registered from reflection and/or scattering mode as before.

The micro/nano-cantilever outlined herein may alternatively be embedded with a magnetic particle/substance such that the application of an oscillating external magnetic field will result in the creation of an oscillation micro/nano cantilever. The oscillating sphere-plane resonance may then be used to monitor conformational changes within a single molecular species as already outlined.

The content of each of the documents referenced in the description are incorporated herein by reference.

The invention will now be illustrated, by way of example, in the following Example.

EXAMPLE

Quartz chips (14 mm in diameter, 0.3 mm thick) were spin-coated with a 50 nm thick layer of gold and then coated with a layer of planar dextran. These gold coated chips were then placed into the fluid cell of a custom built Apertureless Nearfield Scanning Optical Microscope (aNSOM). The fluid cell was then sealed and polymerase buffer was then allowed to flow over the chip.

Immobilisation of the polymerase to the chip surface was carried out according to Jonsson et al., Biotechniques, 1991; 11:620-627. The chip environment was equilibrated with running buffer (10 mM hepes, 10 mM MgCl2, 150 mM NaCl, 0.05% surfactant P20, pH 7.4). Equal volumes of N-hydroxysuccinimide (0.1 M in water) and N-ethyl-N'-(dimethylaminopropyl)carbodiimide (EDC) (0.1 M in water) were mixed together and injected across the chip surface, to activate the carboxymethylated dextran. The polymerase (RB69) (150 μl at 400 nm) was mixed with 10 mM sodium acetate (100 μl, pH 5) and injected across the activated surface. Finally, residual N-hydroxysuccinimide esters on the chip surface were reacted with ethanolamine (35 μl, 1 M in water, pH 8.5), and non-bound polymerase was washed from the surface. The immobilization procedure was performed with a continuous flow of running buffer (5 μl/min) at a temperature of 25 degrees Celsius.

In order to detect polymerases and conformational/energy changes taking place within said polymerases, a gold coated AFM cantilever was used in tapping mode. A beam of a CW He—Ne laser was focused on the gold cantilever. Light scattered from the gold cantilever tip was then coupled into a double monochronometer and then into a detection Photomultiplier Tube (PMT) connected to a computer.

In order to detect non-polymerizing polymerases, an initial scan was carried out over the chip surface with the aSNOM tip without nucleotides in the running buffer. Once a single immobilized polymerase was detected, the intensity peak of the scattered light radiation (scattered intensity v distance from surface) was measured while the aNSOM was operated in stationary mode.

Next, the polymerizing value was determined by the following steps:

Two oligonucleotides were synthesized using standard phosporamidite chemistry. The oligonucleotides defined as SEQ ID NO.1 was used as the target polynucleotide, and the oligonucleotides defined as SEQ ID NO.2 was used as the primer.

```
CAAGGAGAGGACGCTGCTTGTCGAAGGTAAGGAA   SEQ ID NO. 1
CGGACGAGAGAAGGGAGAG

CTCTCCCTTCTCTCGTC                    SEQ ID NO. 2
```

The two oligonucleotides were reacted under hybridizing conditions to form the target-primer complex. The primed DNA was then suspended in buffer (20 mM Tris-HCL, pH 7.5, 8 mM MgCl2, 4% (v/v) glycerol, 5 mM dithiothreitol (DDT).

Whilst the AFM tip is still in stationary mode, the pre-primed complex was then injected into the flow cell at a flow rate of 500 µl with 0.4 mM of all four nucleotides (dATP, dTTP, dGTP, dCTP). Immediately after the second injection, the change in resonant intensity was recorded. The change in peak position was recorded, indicating a change in refractive index due to polymerase activity. This shows incorporation of the nucleotide.

(iii) detecting a change in dielectric constant during or after the reaction, to thereby detect a change in the conformational or energetic state of the molecular species.

2. The method according to claim 1, wherein the molecular species is immobilized to a solid support.

3. The method according to claim 1, wherein the molecular species is a protein.

4. The method according to claim 1, wherein the molecular species is a polynucleotide processive enzyme.

5. The method according to claim 4, wherein a conformational change results from the interaction of the enzyme with a target polynucleotide.

6. The method according to claim 4, wherein the enzyme is a polymerase.

7. The method according to claim 6, wherein incorporation of each of the nucleotides A, T (U), G and C causes a characteristic change in the energetic state/conformation of the polymerase.

8. The method according to claim 1, wherein the localized area of electromagnetic field enhancement is created by positioning the molecular species between first and second electrodes and applying an electrical signal to the first electrode.

9. The method according to claim 8, wherein the first and second electrodes are spaced between 1 nm and 1mm apart.

10. The method according to claim 8, wherein the electrical signal is an AC voltage of predetermined frequency.

11. The method according to claim 10, wherein the frequency is between 1 Hz and 100 GHz.

The invention claimed is:

1. A method for detecting a change in the conformational or energetic state of a molecular species during or after a reaction, comprising the steps of:
   (i) immobilizing the molecular species, under conditions suitable for the reaction to occur;
   (ii) contacting at least part of the molecular species with a localized area of electromagnetic field enhancement; and 12. The method according to claim 8, wherein a change in the conformational or energy state of the molecular species is detected by measuring a change in the impedance of the electrodes.

13. The method according to claim 8, wherein a change in the conformational or energy state of the molecular species is detected by measuring a change in the total capacitance of the electrodes.

14. The method according to claim 13, wherein the capacitance is measured using an AC bridge.

15. The method according to claim 1, wherein the localized area of electromagnetic field enhancement is created by an integrated plasmon wave concentrator, microfabricated on a metal layer capable of supporting surface plasmons.

16. The method according to claim 15, wherein the plasmon wave concentrator comprises a sub-wavelength aperture surrounded by at least one linear groove, with dielectric layers above and below.

17. The method according to claim 16, wherein the at least one linear groove is situated on both the upper and reverse sides of the metal layer.

18. The method according to claim 16, wherein a change in the conformational or energy state of the molecular species is detected by creating a visible or infra-red laser incident to the metal layer(s) and measuring a change in the intensity of the light emitted from the sub-wavelength aperature.

19. The method according to claim 16, wherein a change in the conformational or energy state of the molecular species is detected by creating a visible or infra-red laser incident to the metal layer(s) and measuring the phase shift of light emitted from the sub-wavelength aperture as it passes through a concentrator structure.

20. The method according to claim 16, wherein a change in the conformational or energy state of the molecular species is detected by creating a broad-band electromagnetic beam incident to the metal layer(s) and measuring a change in the wavelength of light emitted from the sub-wavelength aperature.

21. The method according to claim 1, wherein the localized area of electromagnetic field enhancement is created by a metalized scanning probe microscope or atomic force microscope tip, on a surface plasmon supporting surface.

* * * * *

```
SEQUENCE LISTING

<160> NUMBER OF SEQ ID NOS: 2

<210> SEQ ID NO 1
<211> LENGTH: 53
<212> TYPE: DNA
<213> ORGANISM: Artificial Sequence
<220> FEATURE:
<223> OTHER INFORMATION: Sample Target Polynucleotide

<400> SEQUENCE: 1
caaggagagg acgctgcttg tcgaaggtaa ggaacggacg agagaaggga gag        53

<210> SEQ ID NO 2
<211> LENGTH: 17
<212> TYPE: DNA
<213> ORGANISM: Artificial Sequence
<220> FEATURE:
<223> OTHER INFORMATION: Sample Primer

<400> SEQUENCE: 2
ctctcccttc tctcgtc                                                17
```